United States Patent [19]

Landau

[11] Patent Number: 5,782,802
[45] Date of Patent: Jul. 21, 1998

[54] MULTIPLE USE NEEDLE-LESS HYPODERMIC INJECTION DEVICE FOR INDIVIDUAL USERS

[75] Inventor: Sergio Landau, Laguna Niguel, Calif.

[73] Assignee: Vitajet Corporation, Laguna Hills, Calif.

[21] Appl. No.: 792,574

[22] Filed: Jan. 30, 1997

Related U.S. Application Data

[63] Continuation-in-part of Ser. No. 621,080, Mar. 22, 1996, abandoned.

[51] Int. Cl.$^6$ .................................................. A61M 5/30
[52] U.S. Cl. ......................................... 604/68; 604/72
[58] Field of Search ........................... 604/68, 72, 148, 604/218, 244, 415, 241, 242

[56] References Cited

U.S. PATENT DOCUMENTS

| | | | |
|---|---|---|---|
| 3,057,349 | 10/1962 | Ismach | 128/173 |
| 3,526,225 | 9/1970 | Isobe | 128/173 |
| 3,859,996 | 1/1975 | Mizzy et al. | 128/173 |
| 3,908,651 | 9/1975 | Fudge | 128/173 |
| 4,266,541 | 5/1981 | Landau | 128/207 |
| 4,342,310 | 8/1982 | Lindmayer et al. | 128/207 |
| 4,592,742 | 6/1986 | Landau | 604/71 |
| 4,874,367 | 10/1989 | Edwards | 604/72 |
| 4,913,699 | 4/1990 | Parsons | 604/68 |
| 4,966,581 | 10/1990 | Landau | 604/72 |
| 5,062,830 | 11/1991 | Dunlap | 604/68 |
| 5,073,165 | 12/1991 | Edwards | 604/72 |
| 5,312,335 | 5/1994 | McKinnon et al. | 604/72 |
| 5,334,144 | 8/1994 | Alchas et al. | 604/68 |

FOREIGN PATENT DOCUMENTS

WO95 03844  2/1995  WIPO.

*Primary Examiner*—Gary Jackson
*Attorney, Agent, or Firm*—Terry L. Miller

[57] ABSTRACT

A multiple use needle-less hypodermic injection device for individual users comprising of a light weight, pocket sized, spring powered unit, and a multiple use, low cost, easily replaceable thermoplastic injection head. The present invention targets the single-patient-self-injection applications, such as insulin users, when risks of cross contamination between different patients are not present, therefore not requiring the parts containing the medicament dose, or the parts in contact with the delivery of the medicament dose, to be necessarily disposed and replaced after each injection. The low cost plastic injection head is easily refilled by the user without dismounting from the spring powered unit, by means of an adaptor that can be attached to a standard medicament vial, or alternatively, by means of a custom made pre-filled vial which connects directly to said injection head, therefore allowing the low cost thermoplastic injection head to be refilled and used several times without necessarily having to be disposed or removed from the power unit after each injection.

15 Claims, 11 Drawing Sheets

MULTIPLE USE NEEDLE-LESS HYPODERMIC INJECTION DEVICE FOR INDIVIDUAL USERS

Cross Reference to Related Application

This application is a Continuation-in-Part of U.S. patent application Ser. No. 08/621,080, filed 22 Mar. 1996 now abandoned.

BACKGROUND OF THE INVENTION

1. Field of the Invention

The present invention relates generally to a needle-less hypodermic injection device, and particularly to a self injection device with a low-cost, multiple-use disposable injection head for individual users. Discussion of the Prior Art Needle-less hypodermic injection devices have been in commercial use for over 40 years. Initially hypodermic jet injectors were invented to speed up the process of injecting multiple patients in a situation, such as, a vaccination campaign in which numerous patients were subsequently injected with the same vaccine. The prior art includes inventions such as Ismach, U.S. Pat. No. 3,057,349; Isobe, U.S. Pat. No. 3,526,225; Mizzy, U.S. Pat. No. 3,859,996; and Landau, U.S. Pat. No. 4,266,541.

These inventions are any longer considered safe by today's standards. However, needle-less hypodermic injection devices for multiple use are still considered by official health organizations as a safe and reliable means of delivery of certain medications, provided that all parts in contact with the fluid path are disposed after each injection. That is, for devices that are meant to inject medication on different people, if the nozzle tip touches the patients' skin, it is believed today by public health organizations that the possibility of transferring viruses such as HIV and Hepatitis B from one patient to another exists and may be significant. It is considered that replacing the nozzle tip alone after each injection is not sufficient to guarantee complete elimination of cross contamination between patients, since by particles of blood ref lux during the injection, viruses or pathogens may be carried on to the inside of the dose chamber, and therefore contaminate the following medication dose to be injected in the next patient.

Accordingly, in case the same needle-less device is used on different patients, the only "absolute" means to completely avoid cross contamination of diseases is either: a) sterilizing all parts in contact with the dose medication path after each injection, or; b) disposing of all parts in contact with the dose medication path after each injection. The first alternative is too time consuming and absolutely not practical in today's health care industry. The second alternative based on today's technology, has not proven to be cost effective for most vaccines and drugs commercially available in the marketplace.

On the other hand, there are the needle-less injection devices that are meant to be used by a single patient in therapies that require frequent hypodermic injections of certain drugs. Among these frequent, repetitive, and long term injectable drugs are insulin, growth hormones, interferon for cancer treatment, drugs for migraine headaches, allergy reduction compounds, drugs for male erection disfunction, birth control injectable drugs, and many others. Since these hypodermic injectable therapies are long term (i.e., some of them for the entire life of the patient), each needle-less hypodermic device is usually used and owned by only one person, in which case it is not medically justifiable for the parts in contact with each dose medication to be sterilized or disposed after each injection.

It is generally accepted by official health institutions, including the U.S. Food and Drug Administration that if a needle-less hypodermic device is to be used by only one person, the injection head or the parts in contact the medicament dose will have to be cleaned and disinfected every 15 days. The prior art includes some inventions such as Fudge, U.S. Pat. No. 3,908,651; Lindmayer et al., U.S. Pat. No. 4,342,310; and Landau, U.S. Pat. No. 4,592,742, that describe devices that have a reusable or permanent injection head. These devices however, require the users to periodically disassemble the injection head for the necessary cleaning, unclogging and disinfection. These procedures are time consuming and require a certain skill from the users.

In order to guarantee sterility, avoid the risk of cross contamination and reduce user's handling of the drug, in the recent years, the concept of single-use disposable medicament dose has been brought to the needle-less hypodermic injection devices. The prior art contains several inventions that describe needle-less devices with disposable single-dose medicament containers or cartridges. Among these inventions are the ones in which the drug is pre-filled and the entire needle-less device is single-use and disposed of after each injection, such as Parsons, U.S. Pat. No. 4,913,699; Alchas et al., U.S. Pat. No. 5,334,144; and Weston, Wyo. 95/03844. Other inventions such as Landau, U.S. Pat. No. 4,966,581; Dunlop, U.S. Pat. No. 5,062,830; and Edwards, U.S. Pat. No. 5,063,165, comprise of devices in which only the cartridge containing the pre-filled medicament dose is disposed of after each use. McKinnon, U.S. Pat. No. 5,312, 335, describes a device that comprises a needle-less syringe that may be filled manually by the user, outside the gas powered unit. McKinnon's needle-less syringe is also designed to be single-use as, once a single injection is over, the syringe has to be necessarily removed from the gas powered unit.

These inventions comprising disposable single-use needle-less injection devices, or needle-less devices that utilize single-use disposable medicament cartridges, have one main limitation for their wider commercial use. This limitation is the high cost per medicament dose involved in the disposal of these materials. Today, the medicament dose cartridges, or needle-less injection heads can be made from thermoplastics which are significantly less expensive than stainless steel generally used in reusable needle-less injection heads, but which are still quite expensive to be disposed after each and every injection.

In contrast, disposable syringes are widely commercially available and widely used, but the thermoplastic materials they are made of barely have to support any mechanical stress. Several medicaments are also provided in single dose vials that are disposed of after use. However, the materials and manufacturing processes employed in the disposable syringes and disposable glass vials allow high production volume at very low costs.

Unlike disposable syringes, and disposable glass vials, needle-less cartridges are subject to high pressures during the injection. The parts of a disposable needle-less cartridge or a disposable needle-less injection head have to be made of high quality engineering thermoplastics. Also, these injection heads require parts designed with thick walls in order to support the mechanical stress developed during a needle-less injection. For this reason, these parts are also more difficult to be molded. All these factors combined raise the manufacturing cost of any single dose medicament container that is ready for use in a needle-less device, and in most cases, do not render themselves commercially viable.

SUMMARY OF THIS INVENTION

The device which is the object of this invention will place itself between the single-user, needle-less injection devices with reusable injections heads; and those other needle-less injection devices designed for partial or complete disposal after each injection.

The present invention solves respectively the problems of both concepts explored by the prior art, which do not really address the need of those patients who repetitively have to inject themselves with a certain medicament, such as the persons with diabetes that are insulin dependent. The present invention is meant for this type of user. It eradicates the two main limitations of each of the concepts known by the prior art, which respectively are:

a) the constant disassembling, cleaning and disinfection of the devices with reusable injection heads; and b) the high cost per medicament dose of the single use disposable needle-less injection heads, which necessarily have to be made of a good mechanical performance thermoplastic.

Like the single-use needle-less injection devices, this invention device also utilizes an injection head made of good mechanical performance thermoplastics. But unlike the single cartridge devices, this invention provides the design means and elements to allow its injection head to be easily refilled and reused by the user with the proper amount of medicament the user will require at each time.

On the other hand, unlike the reusable needle-less injection devices which require disassembly, cleaning and disinfection every 15 days, this invention provides the users with the means to easily, quickly and economically remove the injection head, discard it, and replace it for a new one, every 15 days.

This invention for its use by a user comprises basically of:

a) an injection head comprising a transparent thermoplastic generally cylindrical nozzle and a thermoplastic piston tip, both supplied to the user in a sterile pack;

b) a spring powered unit, with means to quickly attach and detach the injection head from this spring powered unit; and c) a pre-filled special vial which connects to the injection head, or alternatively an adaptor which is attached to a commercially available vial.

DESCRIPTION OF THE PREFERRED EMBODIMENTS OF THE INVENTION

The spring powered unit of the present invention works in a very similar way to the prior art described In Landau U.S. Pat. No. 4,592,742.

Figure 1:
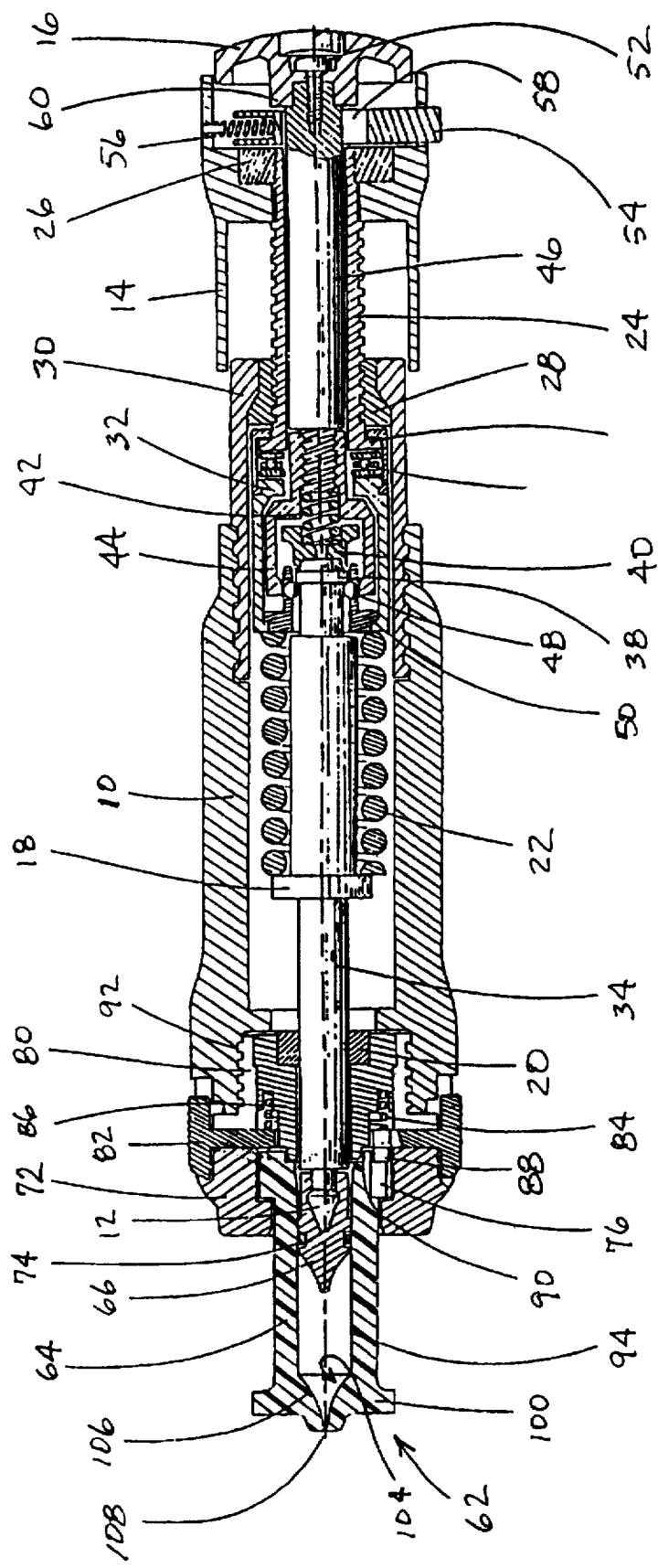
FIG. 1 is a cross section view of the needle-less injection device with the injection head already mounted on its front end.

FIG. 1 shows a longitudinal cross section of a mechanism for a spring powered unit according to the present invention, and is already prepared to make an injection. A piston tip of the injection head is shown moved axially to its full retracted position, creating a chamber within a nozzle of the injection head for receiving a dose of medicament to be injected, as will be further explained. In the description below, "forward" and similar terms refer to a direction toward the left-hand side of FIG. 1 (i.e., toward the person who is injected with medicament using the device). Conversely, "rearward" and similar terms indicates a direction toward the right-hand end of FIG. 1.

Figure 2:
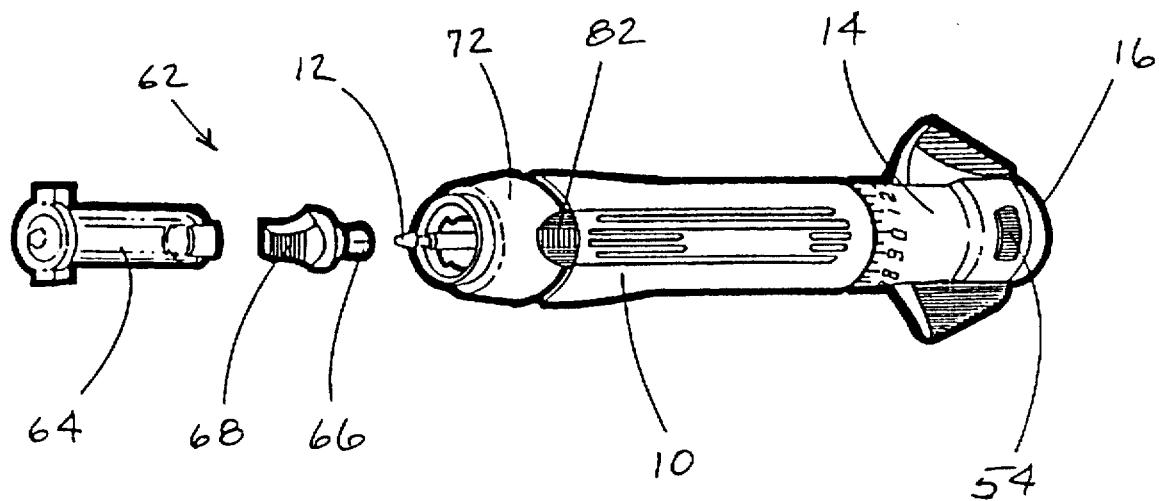
FIG. 2 is a perspective view of the needle-less injection device with a separate injection head before it is mounted on the power unit.

FIG. 2 includes an exploded perspective view of the whole spring powered unit 10 with injection head installed. Basically, the mission of the spring powered unit 10 is to apply back and forth movements to the ram's tip 12, at which the piston tip is carried. On the one hand, the back and forth movements are produced at low speed in order to fill the chamber within the nozzle, and allow for adjustment for the correct medicament dose, in which case these movements are controlled by the user when the dosage drum 14 is turned clockwise or counterclockwise. On the other hand, the forward movement of the ram's tip 12 will also be produced at high speed, when button 16 is pressed by user and the injection is given. In order to allow these movements of the ram's tip 12, it is first necessary to wind or cock the spring powered unit 10.

FIG. 1 shows a cross section of the entire mechanism of the spring powered unit in the position ready to be discharged and the injection given. It is important to note that the nozzle (to be further described below) at the portion of this nozzle which defines the chamber receiving medicament which is to be injected, and which is transparent, is completely exposed for viewing by the user. Thus, the chamber and medicament therein is completely exposed for visual inspection by the user prior to injection. Moreover, the user can see into the chamber within this nozzle to verify that there are no air bubbles in the liquid medicament about to be injected.

In order to place the mechanism in this condition, initially, the ram's shoulder 18 is all the way forward, leaning against the fixed shock absorber 20, and the main spring 22 is decompressed at its initial preload position. The dosage drum 14 is fixed to the threaded sleeve 24 by means of a threaded washer 26. Therefore, as the dosage drum 14 is turned clockwise by the user, the threaded sleeve 24 moves forward through the threads of the bushing 28 which is fixed to the rear body 30 of the spring powered unit 10. The threaded sleeve 24 is permanently connected to the discharge mechanism 32, the functioning and operation of which will be detailed later on. As the whole discharge mechanism 32 moves forward, pushed by the threaded sleeve 24, it compresses forward the spring 22 against the shoulder 184 which is still leaning against the fixed shock absorber 20. The ram 34 has on its rear end a neck 36 and a smaller shoulder 38. As the dosage drum 14 reaches its forward end of its stroke, the discharge mechanism 32 advances forwards over the ram's rear end, which consequently pushes backwards the discharge spring cap 40, compressing the discharge spring 42. The bushing 44 is threaded and connected to the discharge shaft 46.

When the discharge spring 42 is compressed backwards, it forces the bushing 44 and the discharge shaft 46 to move backwards as well. The ball bearings 48 are inside radial holes symmetrically disposed along the circumference of the cylindrical shaped sleeve 50, and these ball bearings 48 are maintained in place inside these holes by the inner face diameter of bushing 44 and by the outer face diameter of spring cap 40. As spring cap 40 and bushing 44 move backwards, the ball bearings 48 are pushed inward against ram's neck 36 by the tapered inner front end of the bushing 44. As they move inward, the ball bearings 48 are trapped in between the ram's rear neck 36 and the inner front end of the bushing 44. In this position, the ball bearings 48 lock the ram 34 to the discharge mechanism 32, since the ram's rear small shoulder 38 at the neck 36 cannot pass through ball bearings 48, even though the main spring 22 is now fully compressed and forcing ram 34 and discharge mechanism 32 apart from each other. Once the ram 34 is attached and locked to the discharge mechanism 32, the dosage drum 14 may be rotated counterclockwise by the user, consequently moving backwards the threaded sleeve 24, the discharge mechanism 32, the fully compressed main spring 22, and the ram 34. As will be explained below, this backward movement of the ram and piston tip is used to fill the device with medicament for injection.

As shown by FIG. 1, the ram 34 is locked to the discharge mechanism 32, and the main spring 22 is fully compressed. As explained above, to achieve this position, the discharge shaft 46 has moved backwards pushed by discharge spring 42. The discharge shaft 46 is permanently attached to the discharge button 16 by means of a small screw 52. Therefore, when the discharge shaft 46 moves backwards, the button 16 moves backwards as well, allowing safety latch 54 to automatically slide in between button 16 and dosage drum threaded washer 26, pushed by safety latch spring 56. In this position, if the button 16 is accidentally pushed, the button's forward inner face 60 will be pressed against the safety latch 54 and the device will not discharge. Consequently, the button 16 will not be allowed to move forward since the safety latch will be blocking its way. The ram 34 will then continue to be locked to the discharge mechanism 32. In order to discharge the device, the bushing 44 has to move forward allowing the ball bearings 48 to move outward, away from the ram's neck 36, which consequently allow the ram's rear shoulder 38 to pass through, pushed vigorously by the fully compressed main spring 22. The bushing 44 will move forward only if the button 16 moves forward as well, since they are connected to each other by the discharge shaft 46. Since the button 16 is blocked by the safety latch 54, the device cannot be discharged, preventing this way accidental injections.

In order to allow discharge, the safety latch 54 has to be manually pushed laterally by the user against the spring 56, so that the safety latch hole 58 is aligned with the button's forward inner face 60. In the position the safety latch 54 would not be blocking button 16 to move forward. By keeping the safety latch 54 pressed in, the user then can press the button 16 to discharge the device and give the injection.

All other figures from 2 through 7c show in detail how the injection head, referred to with reference numeral 62, interfaces with the spring powered unit, the medicament container, and the user.

FIG. 2 shows the order the injection head components are mounted on the spring powered unit. The injection head, comprising of nozzle 64, piston tip 66 and protective cap 68, is provided to the user in a sterile pack. The piston tip is provided protected by the cap 68, so that user does not touch the sterile piston tip 66 with his fingers while mounting the injection head on the spring powered unit.

Figure 3:
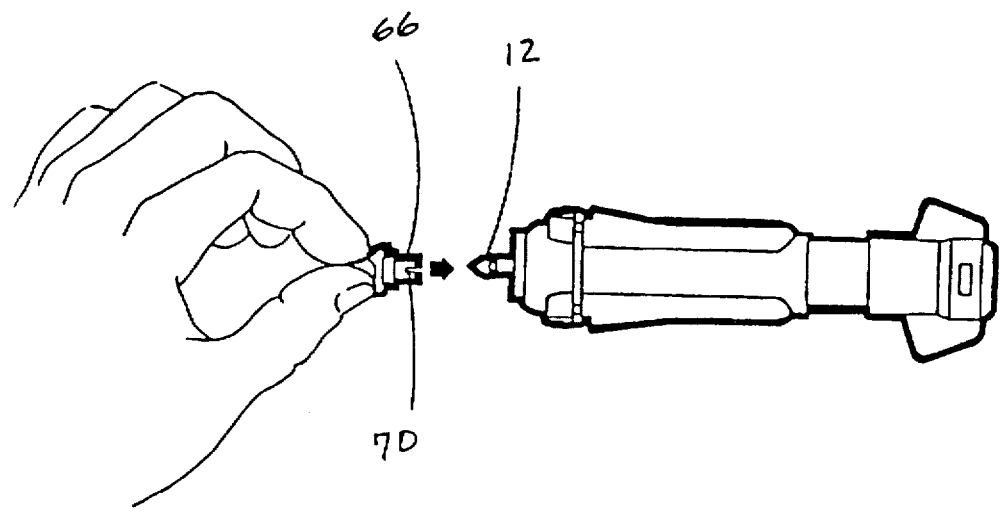
FIG. 3 is a side elevation view of the needle-less device with the piston tip being inserted by user.
Figure 3A:
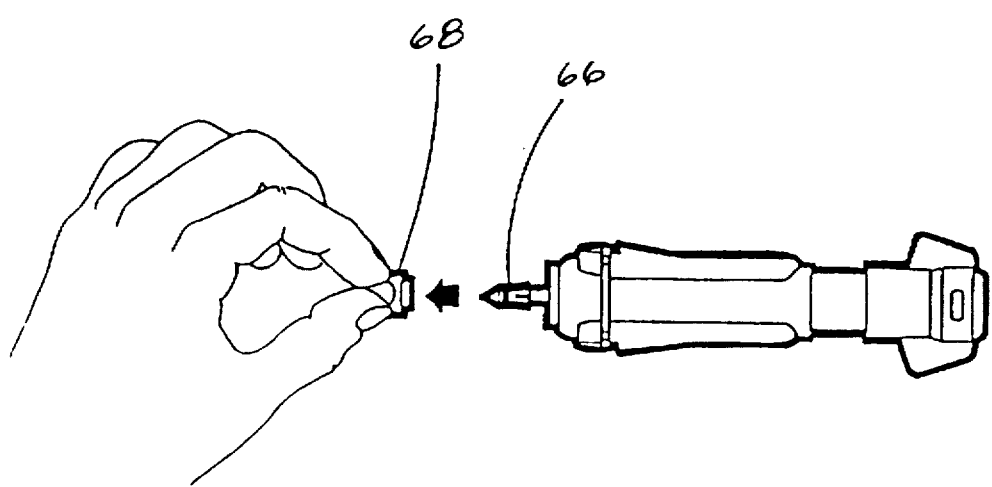
FIG. 3a is a side elevation view of the needle-less device with the piston tip already inserted in the ram and the protective cap being removed.

FIG. 3 and FIG. 3a show the procedure of inserting the piston tip 66 on the ram's tip 12. The rear end of the piston tip 66 has an inner shape that matches with the conical shape of the ram's tip 12, as shown in FIG. 1. The piston tip is made of flexible and high impact thermoplastic, such as Polycarbonate. The ram 34 is made preferably of stainless steel. When the piston tip 66 is pushed against the ram's tip 12, as shown in FIG. 3, the piston tip's rear end slots 70 stretch out, allowing the piston tip 66 to slide over the ram's conical tip 12 and lock in place.

Figure 4:
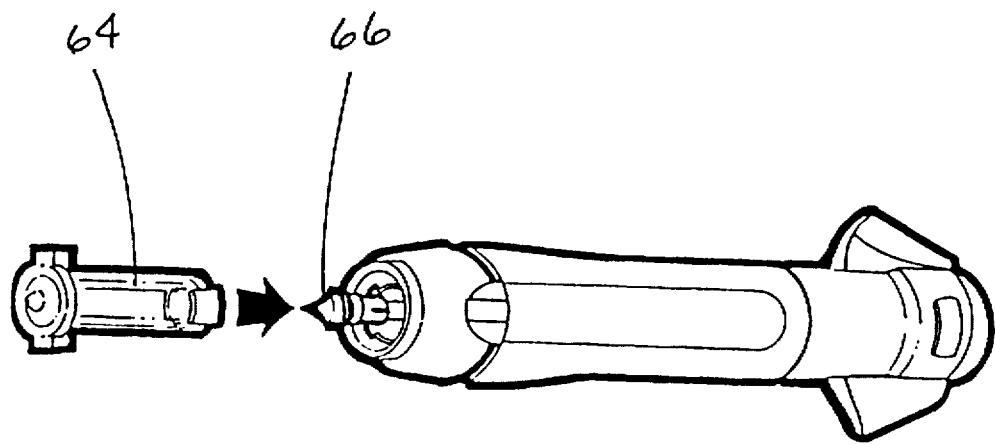
FIG. 4 is a perspective view of the needle-less device with the cylindrical nozzle being inserted over the piston tip.
Figure 4A:
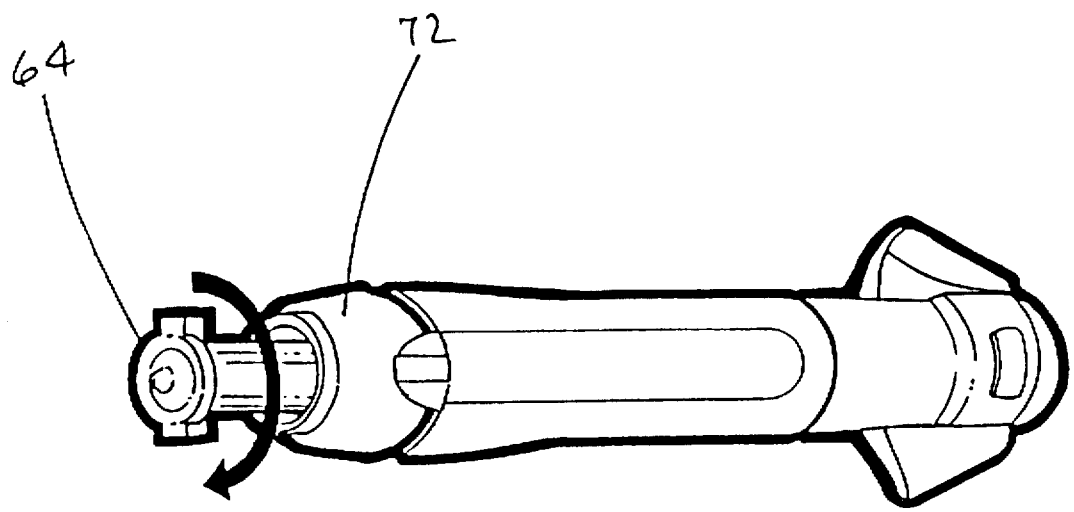
FIG. 4a is a perspective view of the needle-less device with the cylindrical nozzle being locked in the spring powered unit.

As show in FIG. 2 and FIG. 3, the protective cap 68 has two opposed surfaces with generally a concave ribbed shape in order to allow easy manual handling and firm grip with the fingers when the user is inserting the piston tip 66 over the ram's tip 12. As shown in FIG. 3a, the protective cap 68 is pulled out and disposed of, once the insertion is over. This way, the user never touches the piston tip 66 and preserves sterility during the insertion process. Once the piston tip 66 is attached to the ram's tip 12, the cylindrical nozzle 64 is pushed over the piston tip 66 as shown in FIG. 4. In order to lock the nozzle 64 into the spring powered unit's front connector 72, the nozzle 64 is relatively rotated about 90 degrees.

It is important to mention that the concept of a multiple use injection head, involves providing means to the users to easily install the injection head and secure it in place and, at the same time, provide the absolute assurance that the injection head will not be accidentally removed from its secured position while the medicament vial is attached to or detached from the nozzle 64, or while the device is being filled or discharged. For this matter, the nozzle 64 has to remain secured in place, when any axial, rotational, or transverse forces are applied. The present invention describes a preferred mechanism that addresses this need. This mechanism allows the user to insert and lock the nozzle 64 in its secured position using only one hand, however it requires coordinated action of both of the user's hands in order to remove the nozzle 64 from this secured position.

Figure 2A:
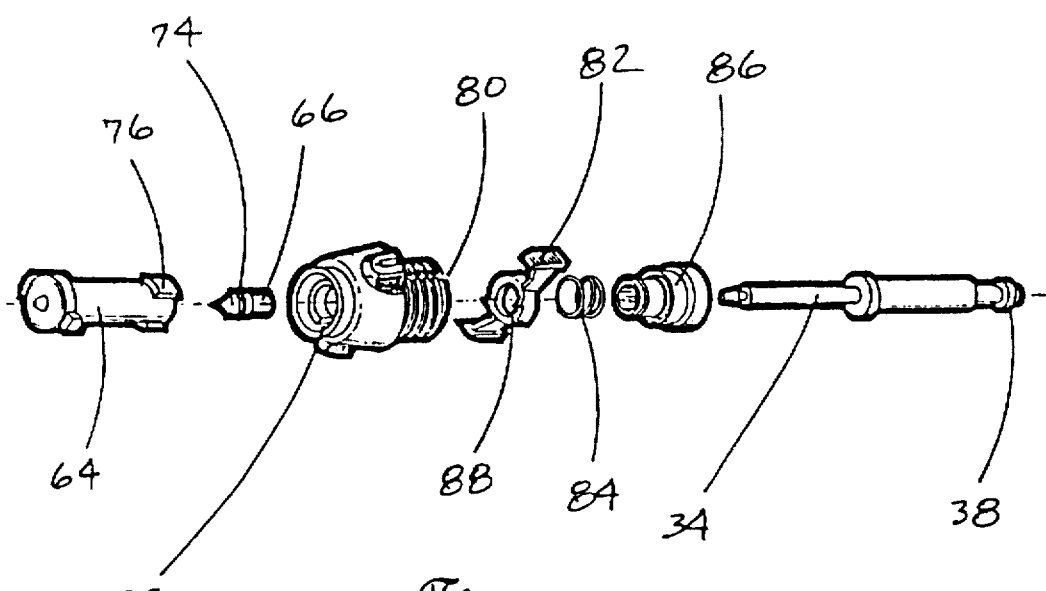
FIG. 2a is an exploded perspective view of all parts involved in the securing and removal of the injection head.

FIG. 2a demonstrates how the securing mechanism for the nozzle 64 works. The insertion of the piston tip 66 has already been explained above. The piston tip's sealing element 74, usually an O-ring, slides inside the nozzle 64, as the nozzle is pushed over the piston tip 66, already installed on the ram's tip 12. The tabs 76 at the rear end of the nozzle 64 have to be aligned with the openings 78 located at the front face of the front connector 72.

On the rear end of the front connector 72, there are two slots 80 in which the nozzle retainer 82 may slide back and forth. The nozzle retainer 82 is kept in the forward position by the retainer spring 84 compressed between the nozzle retainer 82 and the ram's bushing 86 which is permanently fixed to the front connector 72. The nozzle 64 may be pushed backwards, sliding over the piston tip 66, until the rear face of nozzle 64 hits the front face of bushing 86. From that point on, the nozzle 64 cannot be pushed further backwards. As the nozzle tabs 76 are inserted through the openings 78 of the front connector 72, these tabs 76 fall right over the beginning of the ramp side of the retainer bumps 88 located at the center ring of the nozzle retainer 82. As the nozzle 64 is rotated as shown in Fig.4, the tabs 76 slide over the ramp side of the retainer bumps 88 forcing the nozzle retainer to move backwards against the retainer spring 84.

Figure 6:
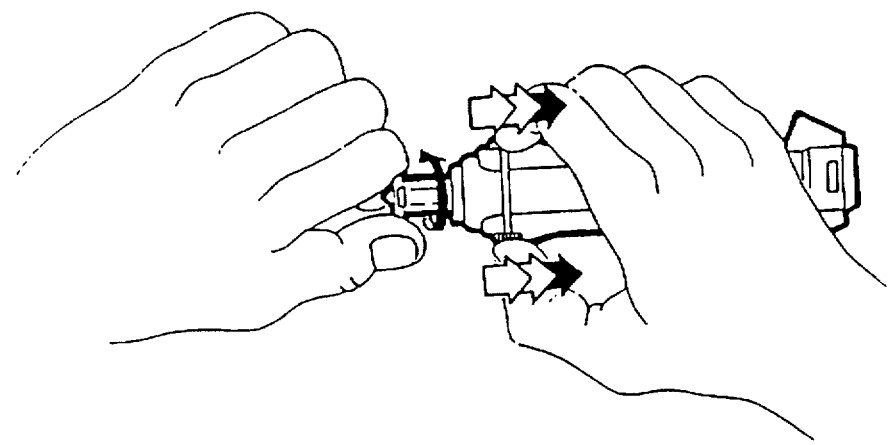
FIG. 6 is an elevation view of the first step of the removal procedure of the cylindrical nozzle.
Figure 6A:
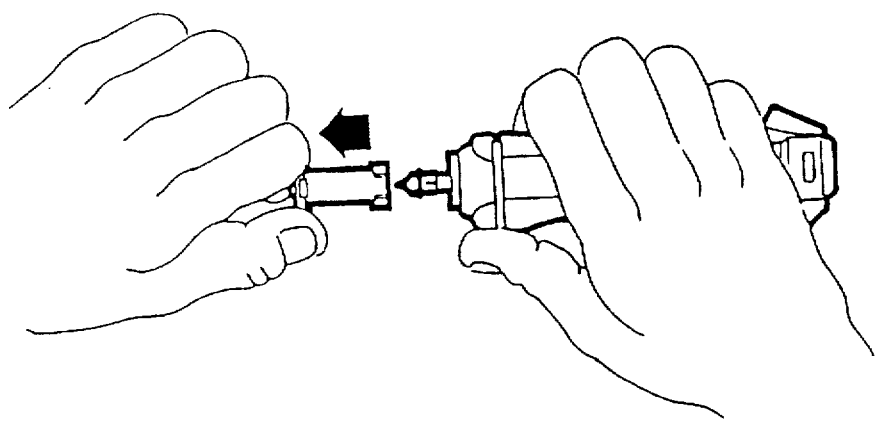
FIG. 6a is an elevation view of the second step of the removal procedure of the cylindrical nozzle.
Figure 6B:
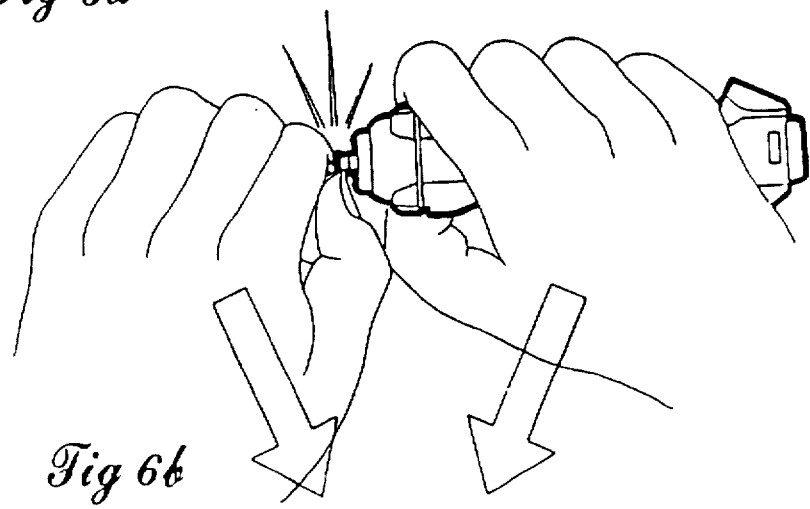
FIG. 6b is an elevation view of the removal procedure of the piston tip.

Once the nozzle 64 is relatively rotated 90 degrees by the user, the tabs 76 would just have gone past the vertex of the retainer bumps 88, to the other side of these bumps, where instead of ramps, there are 90 degree indentations. In other words, the bumps 88 have a sloped side, and a side which extends axially and presents an abutment to the tabs 76. These indentations lock the tabs 76 in place, preventing the nozzle 64 from being rotated. In this position, the nozzle is prevented from being moved back and forth as well, because the tabs 76 are trapped in between the forward inner rim 90 of the front connector 72 and the front face of the bushing 86. The only possible way to remove the nozzle 64 from this secured position is by manually pushing backwards the nozzle retainer 82. In this case, the retainer bumps 88 would retract backwards allowing the nozzle 64 to be rotated until the tabs 76 are again aligned with he openings 78 of the front connector 72. At this point, the nozzle 64 may be pulled out from front connector 72 for removal. This two step nozzle removal is shown by FIGS. 6 and 6a.

Once the nozzle 64 is removed, the piston tip 66 is removed from the ram's tip 12 simply by breaking the piston tip off. The used nozzle and piston tip are disposed of. The used injection head is removed from the spring powered unit to be disposed of and replaced by a new one, at which time the used piston tip 66 may be touched for removal since sterility is no longer an issue.

The front connector 72, the nozzle retainer 82, and the ram's bushing are hollow, allowing the ram 34 to move freely back and forth. This whole assembly is secured to the main body of the power unit 10 by means of a thread 92 shown in FIG. 1.

Figure 5:
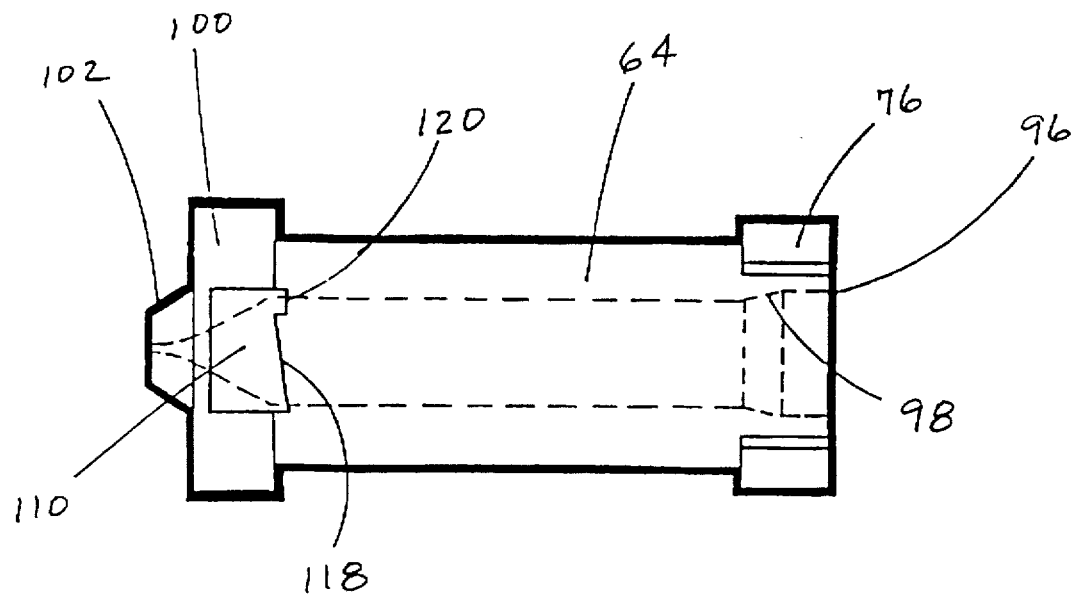
FIG. 5 is a side elevation view of the cylindrical nozzle.
Figures 5A, 5B:
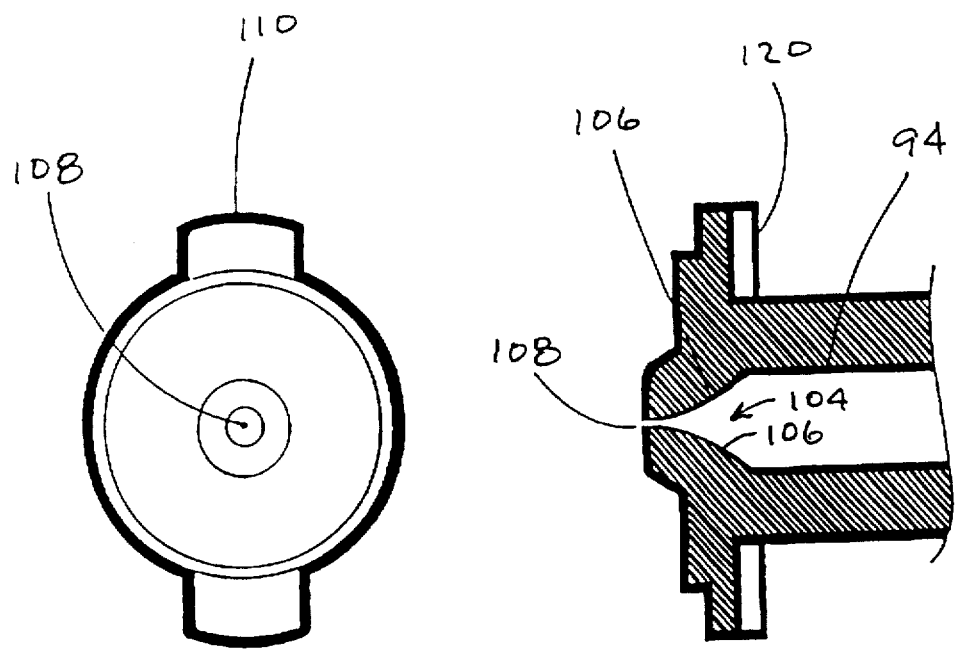
FIG. 5a is an elevation view of the front face of the cylindrical nozzle.
FIG. 5b is a cross section view of the forward portion of the cylindrical nozzle.

FIGS. 5, 5a and 5b show an embodiment of the cylindrical nozzle 64. The cylindrical nozzle 64 is preferably molded in a transparent high impact thermoplastic, such as Polycarbonate, and has a generally tubular shape with its main inner bore 94 having an entrance 96 at the rear end with a diameter slightly larger than the main inner bore 94. The inner bore entrance 96 connects with the front end of bushing 86 when nozzle 64 is inserted into front connector 72. To allow easy and smooth insertion and sliding of nozzle 64 over sealing element 74 of piston tip 66, the inner bore entrance 96 is connected to the main inner bore 94 through a slightly tapered section 98. The front end of nozzle 64 is shaped in form of an integral front end disc 100 with a slight elevation 102 at the center. That is, the disc 100 is an integral end wall of the nozzle 64. The outer diameter of the front end disc 100 is larger than the longitudinal outer diameter of nozzle 64 behind this disc in order to help in resting nozzle 64 on a user's skin and maintaining stability of the needleless device during the injection. A counterbore 104 of the nozzle 64 has a convex shaped section 106 which starts with the diameter of the inner bore 94 and culminates at the front face of nozzle 64 forming the nozzle orifice 108 via which the filling and injection of medicament dose is made.

From its outer cylindrical shape the nozzle 64 has four protruding tabs. Two of these tabs 76 are disposed at the rear end of the nozzle 64, and the other two tabs 110 are located at the front end of nozzle 64. The front and rear tabs of the nozzle 64 are disposed diametrically opposite to one another in pairs, and are preferably at 90 degrees apart from each other at opposite ends of the nozzle 64 in order to allow easy guiding for the user when nozzle 64 is inserted in the front connector's openings 78. The function of the rear tabs 76 has already been explained above. The front tabs 110 which protrude from front disc 100 are used to allow securing and releasing of the adaptor 112 for a standard vial 114, or alternatively, for securing and releasing of a custom-made, pre-filled medicament vial 116, as will be further explained. The front tabs 110 are disposed 180 degrees apart from each other and they protrude flatly at their front face from the outer diameter of disc 100. At their rear face, each tab 110 protrudes from the longitudinal outer diameter of the nozzle 64 in a slightly inclined flat surface 118 which has on one of the edges a small rib 120.

Figure 7:
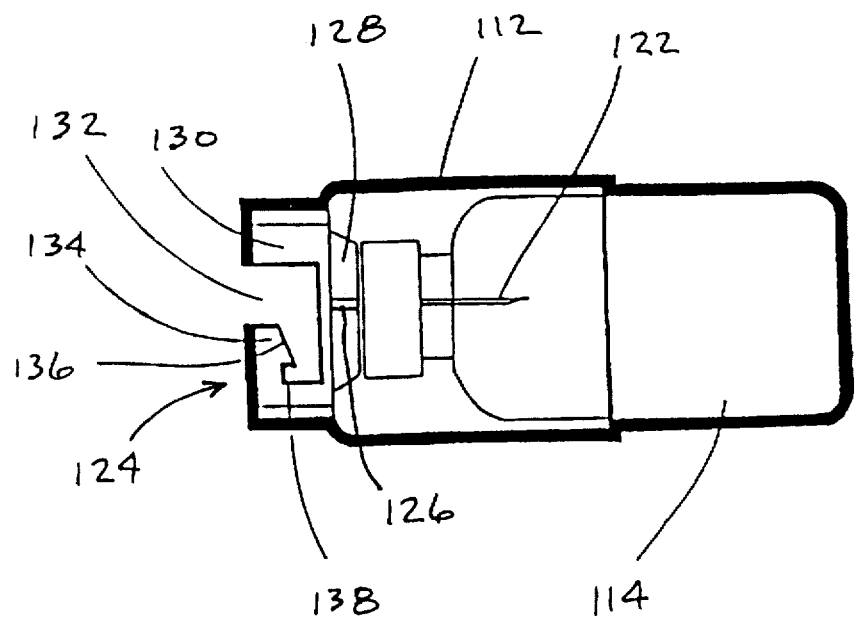
FIG. 7 is an elevation view of the vial adaptor attached to a standard medicament vial.
Figure 7A:
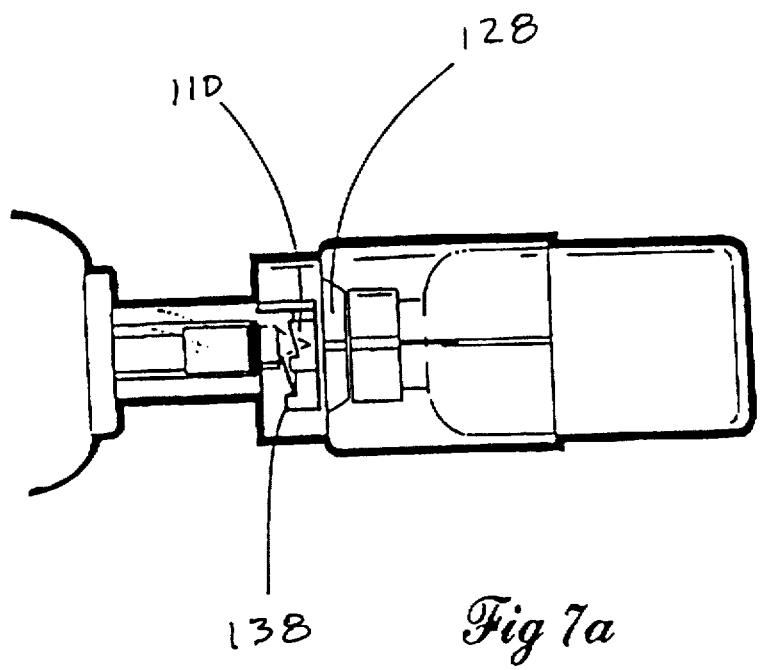
FIG. 7a is an elevation view of the connection between vial adaptor and injection head.

FIG. 7 shows a standard medicament vial 114 inserted into the vial adaptor 112. The vial adaptor 112 is formed by a generally cylindrical thermoplastic transparent body which contains at the center a medicament inlet needle 122 with its beveled tip directed towards the top large opening 124 of the vial adaptor 112 through which the medicament vial 114 is inserted. The bottom end of the inlet needle 122 is connected to the center hole 126 of the elastomeric disc 128, which is usually made out of medical grade silicone. The bottom portion of the vial adaptor 112 has a circular opening 130 with a diameter that will allow the front disc 100 of nozzle 64 to fit in snugly. That is, the front protrusion 102 of nozzle disk 100 sealingly engages this disc 128 when the nozzle 64 is engaged into the adaptor 112 with a push-and-turn motion by the user, as will be seen.

On the circumference of the bottom portion of the vial adaptor 112 there are also two diametrically opposed side openings 132 which will allow the front tabs 110 of nozzle 64 to be inserted. Besides the two side openings 132 there are respectively two arms 134, each one with a slightly inclined inner face 136 and a inner slot 138.

Figure 7B:
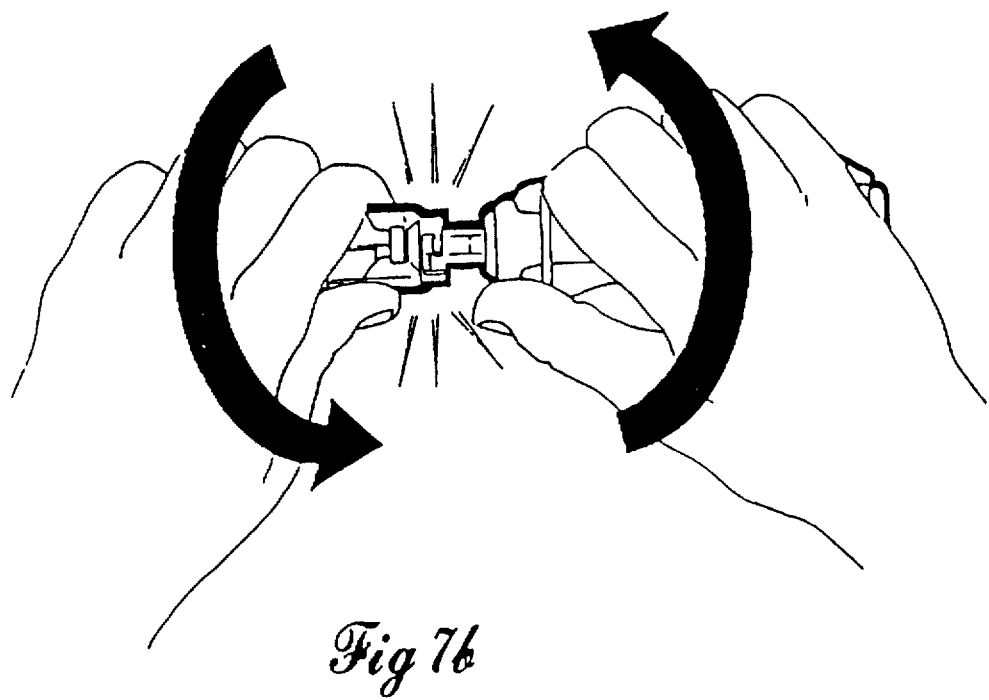
FIG. 7b is an elevation view of the procedure to lock the vial adaptor to the injection head.

When vial adaptor 112 is inserted over the injection head 62, the front end of nozzle 64, which contains orifice 108 within elevation or protrusion 102, compresses the elastomeric disc 54, providing a connecting sealed passage between medicament inlet needle 122 and nozzle's orifice 108. Once vial adaptor 112 is inserted over the injection head, if vial adaptor 112 is rotated in the direction shown in FIG. 7b, the front tabs 110 of nozzle 64 force the two arms 134 to flex outwardly, allowing ribs 120 of front tabs 110 to accommodate in the inner slots 138 of arms 134. Since the front end of nozzle 64 is compressing the elastomeric disc 128, the tension of this elastomeric disc 128 will force the nozzle 64 and vial adaptor 112 apart from each other, therefore forcing the ribs 120 on tabs 110 to remain inside inner slots 138, consequently keeping vial adaptor 120 locked to the nozzle 64 of injection head 62.

Figure 7C:
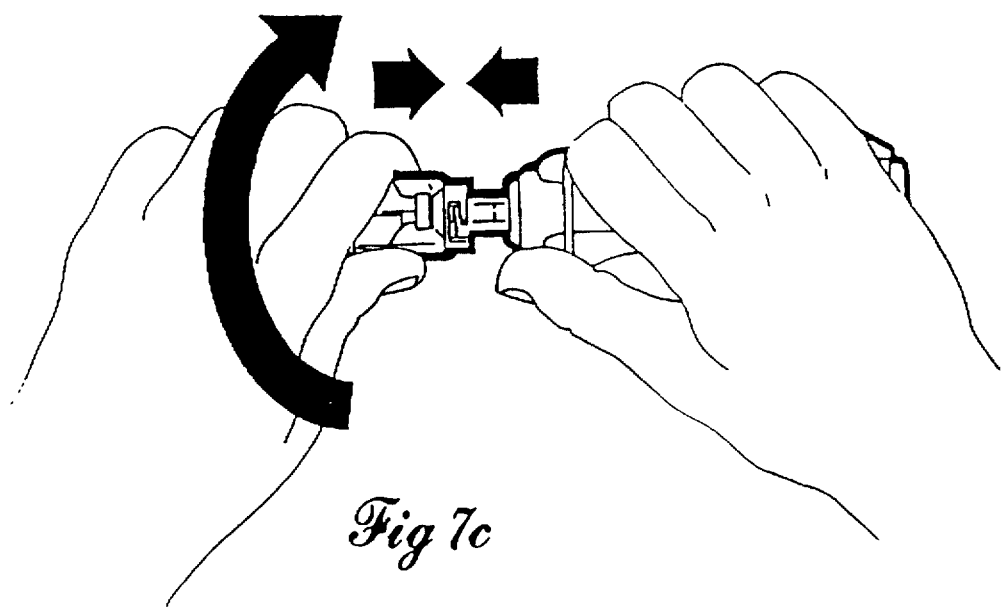
FIG. 7c is an elevation view of the procedure to remove the vial adaptor from the injection head.

The vial adaptor 112 will remains locked to the injection head 62 for filling of proper medicament dose through orifice 108, sucked by the backwards movement of piston tip 66 during the dose filling operation described above. Once the injection head 62 is loaded with the proper dose, the vial adaptor 112 may be removed. To unlock and remove the vial adaptor 112 from the injection head 62, the user will simply push them against each other, compressing further the elastomeric disc 128 in order to release ribs 120 from slots 138. Once these ribs 120 are removed from the inside of the slots 138, the vial adaptor 112 is turned in the opposite direction as show in FIG. 7c, until tabs 110 are again aligned with side openings 132, allowing in this way the vial adaptor 112 to then be removed axially from the injection head 62.

The vial adaptor 112 could be eliminated altogether if the medicaments are provided by drug manufacturers contained in a special vial that is custom-made to be used with the present invention. With the increase of environmental concerns with the disposal of hypodermic needles, the drug manufacturers are increasingly looking into other drug delivery means, including needle-less injection devices. For that matter, some drug manufacturers are already considering packing some of their injectable medicaments into special containers that may or may not be proprietary to a particular device. The present invention includes a preferred embodiment for such custom-made pre-filled medicament vial.

Figure 7D:
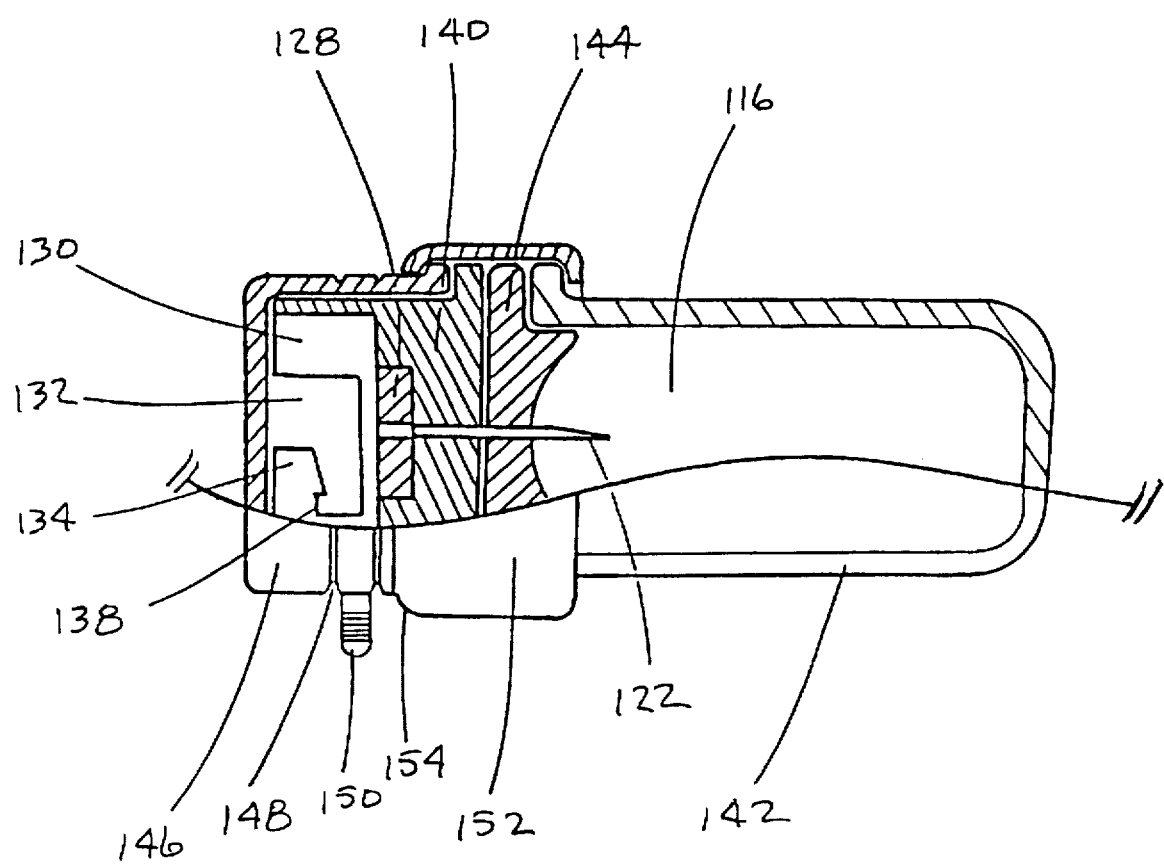
FIG. 7d is an elevation view of the custom made pre-filled vial which may contain one or more doses of medicament.

As show in FIG. 7d, a custom-made pre-filled medicament vial 116 comprises of the same basic design for the connecting elements already described for the vial adaptor 112. The main difference is the fact that these connecting elements are integrated into a thermoplastic head 140 which is press fitted and permanently attached to the medicament glass ampule or vial 142 during the manufacturing process, after this ampule or vial has been pre-filled with the medicament. One of the preferable processes for the manufacturing of such pre-filled medicament vial 116 is to have glass vial 142 filled up with the medicament and then sealed with a standard medical grade rubber stopper 144, both processes can be done by standard automatic drug filling and sealing machines. The pre-filled medicament vial 116 is sealed with a tamper proof plastic cap 146 which is molded with two circular grooves 148 under which the wall of the plastic cap 146 is thinner. The circular section in between the two groves 148 has a tab 150 that protrudes out from the circumference of plastic cap 146. The plastic cap 146 is inserted onto plastic head 140 and both components are then secured to the pre-filled glass vial 142 and stopper 144 by means of a standard vial aluminum cap 152.

As in its conventional use, in this case also, this cap 152 is inserted over glass vial 142. The front end 154 of aluminum cap 152 is then pressed over the edge of plastic cap 146 ensuring that plastic head 140 will be permanently attached to the pre-filled glass vial 142. This process can also be carried out by automatic sealing machines. This way, the whole assembly, which is referred to here as a pre-filled medicament vial 116, becomes a single sealed container which would be unsealed only when the user pulls out tab 150 to rupture plastic cap 146 around the two circular grooves 148. If the pre-filled medicament vial contains more than one medicament dose, the plastic cap 146 can be re-inserted onto the plastic head 140 to maintain pre-filled vial 142 sealed. The whole assembly 116 is discarded once all the medicament contained in the vial 142 is used up by user.

Figure 5C:
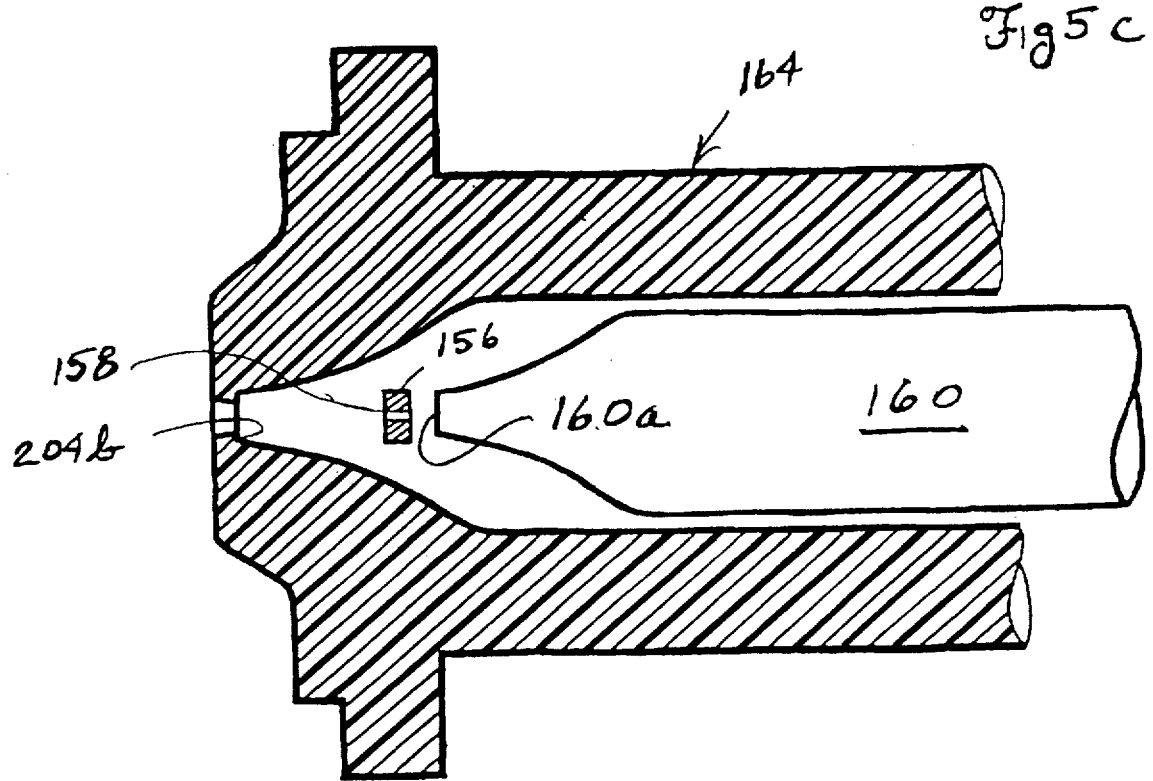
Fig. 5c is a fragmentary cross sectional view of a portion of a cylindrical nozzle according to an alternative embodiment of the invention, and is illustrated at a stage of manufacture during which a high-precision disk orifice is installed in the cylindrical nozzle.
Figure 5D:
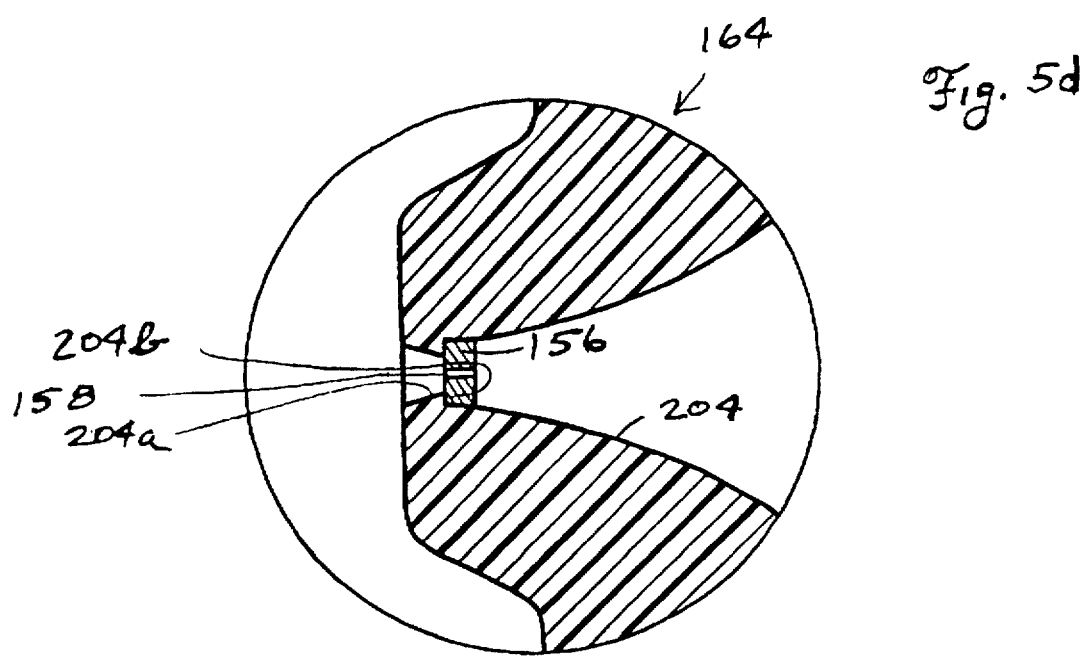
FIG. 5d is an enlarged fragmentary cross sectional view of a portion of the cylindrical nozzle illustrated in FIG. 5c after assembly of this cylindrical nozzle is completed.

FIGS. 5c and 5d show an alternative embodiment of a cylindrical nozzle for use in combination with the other elements of the needle-less injection apparatus described above. This alternative nozzle would be used instead of the nozzle 64. In order to obtain reference numerals for use in describing this alternative embodiment of the nozzle, features which are the same as or analogous in structure or function to features described above are indicated with the same numeral used above, and increased by one-hundred (100). Viewing FIGS. 5c and 5d, it is seen that the cylindrical nozzle 164 is preferably molded in a transparent high impact thermoplastic, such as Polycarbonate, and has a generally tubular shape with its main inner bore 194 having an entrance 196 at the rear end of the nozzle with a diameter slightly larger than the main inner bore 194. As with the nozzle 64 described above, the nozzle 164 includes a front disc 200 with a slight elevation 202 at the center.

In this case, a counterbore 204 of the nozzle 164 has a convex shaped section 206 which starts with the diameter of the inner bore 194 and culminates at the front face of nozzle 164. However, the counter bore 204 includes a stepped-diameter portion 204a cooperating with the adjacent larger-diameter portion to provide a shoulder 204b disposed toward the piston tip 66, recalling the description above. Seated on this shoulder 204b is a orifice disc 156. The orifice disc 156 defines a precisely-formed and dimensioned through hole or bore 158, which provides the nozzle orifice 208 for the nozzle 164. As was the case above, it is from this nozzle orifice 208 from which the injection of medicament dose will be made in the form of a high-velocity liquid jet.

FIG. 5c shows a step in the manufacture of nozzle 164, in which the nozzle orifice disc 156 is inserted into counter bore 204 to be seated on shoulder 204b. Viewing FIG. 5c, it is seen that a plunger 160 is inserted into the counterbore 204 of the nozzle 164. This plunger 160 has a bluff end surface 160a upon which is carried the disc 156. As the plunger and disc are advanced into the counterbore 204 of nozzle 164, the disc 156 is seated onto shoulder 204a.

Importantly, the orifice disc 156 is preferably formed of synthetic gem stone. Particularly, the disc 156 may be formed of synthetic sapphire. In this disc of synthetic sapphire, the through bore 158 is formed, for example, by laser drilling. This laser drilling process for formation of the bore 158 is essentially a thermalforming process. That is, the laser vaporizes the gem stone in its path and provides both a more precise bore 158, and possibly a smaller diameter for the bore 158 than could otherwise be conveniently obtained. Alternatively, the synthetic gem stone may be formed on an elongate mandrel as a tube, which mandrel is then removed before the tube is cut into plural discs 156. In either case, the through passage 158 in the disc 156 is more precise and free of rough surfaces and irregularities than can be obtained by conventional drilling or plastic molding on a fine wire core pin.

Also very importantly, the formation of the bore 158 in this way insures a better and more consistent formation for the entrance opening, exit opening, and through passageway of the bore 158. In contrast to conventional injection nozzles which used a molded plastic nozzle orifice, and which suffer both from low yield in the injection molding process, and from occasions of plastic flash or other malformations of the injection orifice, the synthetic gem stone discs which are used as orifice discs 156 and have thermal-formed fine-dimension bores therein have a very low variability from one to another. Also, the smoothness, consistency, and good fluid flow characteristics of the thermal-formed fine dimension hole 158 of the disc 156 is in contrast to prior metallic orifice members which had a drilled hole, possibly having drilling score marks along the passage of the hole, or flash, or rough edges at one opening or the other. Thus, the nozzle 164 provides a more consistent injection jet velocity between successive nozzles, a better formation of the injection jet, and much improved yield in the injection molding process for the nozzle 164 having the counter bore 204 opening therethrough at a smallest diameter which is much larger than the conventional nozzle orifice diameters. That is, while the conventional nozzles have an orifice of 0.005 to 0.010 inch, which is difficult to mold, the nozzle 164 will have a smallest diameter of the counter bore 204 of about 0.030 inch. Also, in contrast to conventional nozzles which have an inserted metallic orifice member, the nozzle 164 with gem stone disc 156 defining the nozzle orifice (i.e., bore 158) for the nozzle 164, is of a preferable uniformity of bore formation, and never will have any obstructions or malformations (i.e., drilling score marks, drilling chips, or rough edges) to prevent the formation of a good liquid jet during injection.

Figure 8:
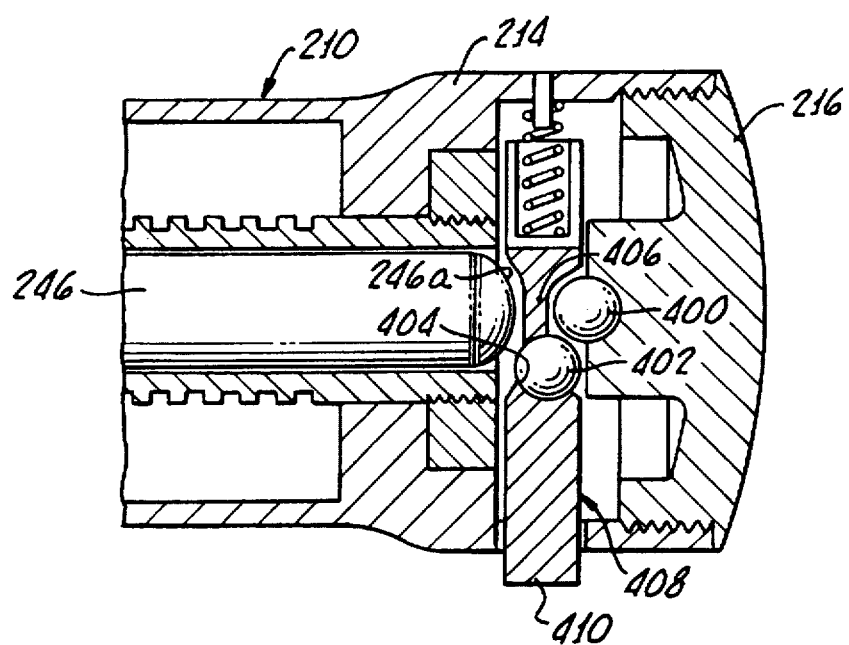
FIG. 8 provides a fragmentary cross sectional view of a portion of an alternative embodiment of the spring power unit.

Turning now to FIG. 8, an alternative construction for the discharge mechanism of the spring power unit 10 is shown. Again, in order to obtain reference numerals for use in describing this alternative embodiment, features which are the same as, or analogous in structure or function to, features described above, are indicated by the same numeral used above, and increased by two-hundred (200). As shown by FIG. 8, the button 216 is in this case fixed in position, being secured to the dosage drum 214 by a threaded engagement therebetween. This button 216 in this case carries a ball member 400. The discharge shaft 246 has moved backwards (i.e., the spring power mechanism is cocked preparatory to making an injection) into confronting relationship at a crowned end surface 246a with another ball member 402. In this position, the axial distance between the surface 246a and the ball member 400 is less than the diameter of ball member 402. The ball member 402 is carried for lateral movement in a hole 404 formed through a web portion 406 of a member 408 with sufficient clearance to allow rotation of the ball member 402. The member 408 has a portion 410 extending outwardly of the dosage drum 214, to provide a push button for discharging the spring power unit. A spring 412 is provided to urge the push button portion of member 408 outwardly, and has a sufficient preload to prevent slight incidental or accidental pressure on button portion 410 from effecting an accidental triggering of the discharge mechanism. Because the ball member 402 is rotational in hole 404, as the push button is depressed by a user and the member 408 moves laterally, the ball member 402 provides a rolling contact between the ball member 400 and the crowned surface 246a.

In the use of the spring power unit 210 illustrated in FIG. 8, the user will prepare the unit as described above. However, discharge of the unit to effect an injection requires only depressing push button 410 to trigger release of the discharge mechanism. These is no safety latch on this embodiment, but experience has shown that users prefer this form of discharge mechanism, and that accidental discharges are very rare. Because the push button 410 does not protrude very far, and requires a deliberate movement to trigger (i.e., a slight incidental or accidental pressure alone on the button 410 will not cause triggering) users are not prone to accidently depressing this button. Thus, accidental discharges of the unit 210 are rare. However, because the unit may be held in the clenched hand against the user's skin, and the button deliberately depressed with the thumb, and with no safety catch to require separate actuation, users are more easily able to inject themselves using this form of trigger mechanism.

Thus, while this invention has been described herein in considerable detail, it is to be understood that it will be apparent to those skilled in the art that numerous modifications may be made herein, without departing from the spirit and scope of this invention.

What is claimed is:

1. For a needle-less injection device, a disposable injection head assembly comprising in combination:

a nozzle member having an elongate generally cylindrical tubular body formed of transparent polymer, said nozzle member including a stepped through bore having a main cylindrical bore portion leading toward an opening at a rear end thereof, and an outwardly tapering portion connecting between the main cylindrical bore portion and an opening of said through bore on the rear end of the nozzle member, which opening is of a diameter greater than said main cylindrical bore portion, adjacent to said rear end said nozzle member including means for releasably mounting to an injection power unit, and at a forward end thereof said nozzle member including a disc-like end wall closing said main bore portion except for a reduced-diameter portion of said through bore opening forwardly through said disc-like end wall and providing a forwardly-directed injection orifice via which liquid medicament is projected forwardly from said nozzle member, said through bore including a tapering counter bore portion extending between said main bore portion and said reduced-diameter through bore portion at said disc-like end wall;

a piston tip member having a forward face portion configured to be received into said counter bore portion of said through bore in conforming relationship thereto, a sealing member disposed rearwardly of said forward face portion sized to slidably and sealingly be received in said main bore portion, and a rearward extension defining means for removable attachment of said piston tip to a ram; and a protective cap member defining a blind bore having an opening and receiving said piston tip with said forward face portion within said blind bore and with sealing engagement of said sealing member upon said cap member to provide environmental protection of said forward face portion in said blind bore, said rearward extension of said piston tip extending outwardly of said blind bore, and said protective cap member outwardly including means for allowing secure manual purchase thereon.

2. The disposable injection head assembly of claim 1 for a needle-less injection device, wherein said nozzle member further carries in said stepped through bore at said disc portion, a synthetic gem stone body having a through bore communicating at each end thereof with said stepped through bore of said nozzle member, and said through bore of said gem stone body defining said injection orifice.

3. The disposable injection head assembly of claim 2 for a needle-less injection device, wherein said gem stone body is formed as a disc having a pair of parallel opposite faces, and said through bore thereof extending through said disc between said pair of opposite faces.

4. A multiple use needle-less injection device comprising:

a housing having a front connector assembly including a forwardly disposed opening for receiving a nozzle member of said injection device, said connector assembly further having a pair of diametrically opposed slots extending axially through said opening and leading to a pair of axially spaced apart opposed circumferentially extending constraint surfaces, said forwardly disposed opening also including a pair of diametrically opposed rear slots at a rear of said connector assembly, a nozzle retainer member slidably received at a pair of outwardly extending arm parts thereof in said pair of rear slots, an outer extent of each of said pair of arms extending outwardly of said connector assembly to present a manually-actuated portion by which said nozzle retainer may be manually moved axially, a central portion of said nozzle retainer presenting a pair of protrusions extending axially toward and aligning generally with said opening of said connector assembly, each of said pair of protrusions on one circumferential side thereof defining a sloping ramp surface leading circumferentially to a cusp and to an axially extending abutment surface, and a resilient member urging said nozzle retainer member axially forwardly toward said opening of said connector assembly; whereby, insertion of a nozzle member having a generally cylindrical body received into said forwardly disposed opening and a pair of radially extending tabs passing along said slots to engage said cusps of said nozzle retainer to move said nozzle retainer axially allowing said tabs to pass axially between said pair of opposed constraint surfaces, relative rotation of said nozzle member causing said tabs to pass circumferentially past said cusp so that said axially extending surfaces of said pair of protrusions engage said pair of tabs and prevent opposite rotation of said nozzle member, and manual axial movement of said nozzle retainer disengaging said axially extending surfaces thereof from said tabs and allowing opposite relative rotation of said nozzle member to align said pair of tabs with said slots and subsequent axial withdrawal of said nozzle member from said opening.

5. A multiple use needle-less hypodermic injection device comprising:

a housing containing a movable ram reciprocable axially along its longitudinal axis, an energy accumulator in said housing and driving said ram forcefully forward, said housing having a connector assembly for receiving an injection nozzle member defining a bore aligned with said movable ram, and a piston tip receivable upon said movable ram for reciprocation within said bore of said nozzle member, said nozzle member having an elongate body formed of transparent polymer material disposed outwardly of said housing, and said bore of said nozzle member extending therethrough along said body to terminate distally generally at an injection orifice, said piston tip in a forward position being disposed adjacent to an end wall of said nozzle member, which end wall carries said injection orifice, and in a second position of maximum spacing from said end wall on said movable ram said piston tip both cooperating with said nozzle body and end wall thereof to define a variable-volume injection chamber for measuring a dose of medicament and defining the most-proximal extent of said injection chamber, said injection chamber being disposed entirely outside of said housing within said nozzle member, whereby said transparent material of said nozzle body allows a user of said injection device to see the entire extent of said injection chamber and medicament therein prior to injection.

6. A nozzle member for a needle-less injection device of the type which confines a quantity of liquid medicament in a chamber cooperatively formed by a piston within a cylinder, and pressurizes this confined liquid medicament by forceful rapid movement of the piston within the cylinder to force the liquid medicament through a fine-dimension injection orifice in the form of a very high speed liquid jet directed toward a recipient thereof and sufficient in velocity and formation to penetrate without confinement of the liquid jet subcutaneously into human skin, said nozzle member comprising:

a nozzle body formed as an elongate cylindrical tubular member having a cylindrical portion forming a cylindrical bore portion for sealing receipt of the piston and cooperating therewith to bound a chamber for receiving the liquid medicament, said nozzle body including an end wall closing one end of said cylindrical bore except for a fine-dimension injection orifice extending therethrough and opening outwardly on said end wall, said end wall including a stepped through bore communicating between said cylindrical bore and ambient outwardly of said end wall, said stepped through bore having a shoulder disposed toward said cylindrical bore portion; and a disc-like orifice member disposed within said stepped through bore and having a pair of opposite parallel faces one of which is seated on said shoulder and the other of which faces said cylindrical bore, said disc-like orifice member a defining a fine-dimension through bore extending between said pair of opposite parallel faces and defining said fine-dimension injection orifice, said orifice member being formed of synthetic gem stone and said fine-dimension through bore being thermal-formed therein.

7. A multiple use needle-less hypodermic injection device comprising:

a main housing containing a movable ram which may be displaced within a predetermined maximum stroke along its longitudinal axis, said main housing having control means on its outside surface to allow a user to move said movable ram back and forth, or to place said movable ram precisely at any position within said maximum stroke, said main housing also having means to allow a user to energize an energy accumulator contained inside said main housing, said main housing also having means to allow a user to activate or suddenly release energy from said energy accumulator, causing said movable ram to move at high speed from a rear position within said maximum stroke to a fixed forward released position;

an injection head containing a piston tip and a generally cylindrical nozzle, said piston tip having means to be securely attached to and detached from the front end of said movable ram, said nozzle having means to be securely attached to and detached from the front end of said main housing, said piston tip having a single use disposable protective cap which allows a user to securely attached said piston tip onto the front end of said movable ram without having to touch said piston tip and to remove the protective cap, said nozzle having a cylindrical inner bore wherein said piston tip, once attached to said movable ram, may slide back and forth respectively pulled back or impelled forward by said movable ram as it moves along its longitudinal axis, said piston tip having a sealing element which seals tight to said nozzle inner bore as it slides in either axial direction along said inner bore, said nozzle having a counterbore leading from said inner bore to a fine-dimension injection orifice, said nozzle also having means to be connected in fluid flow relation to a vial containing liquid medicament so that the injection orifice and counterbore may be use to aspirate medicament into said nozzle inner bore from the vial.

8. The multiple use needle-less injection device of claim 7 wherein said energy accumulator includes a compression spring.

9. The multiple use needle-less injection device of claim 7 wherein said means for securing said piston tip from said movable ram includes said piston tip defining a bore with a rear opening and plural longitudinal slots located at the rear end of said piston tip, said slots allowing the rear opening of said piston tip to flex outwardly to allow the piston tip to be pushed over a conical tip defined on a forward end of said movable ram.

10. The multiple use needle-less injection device of claim 7 wherein said means secure said nozzle to said main housing includes a nozzle retainer movable within said main housing, said nozzle retainer having a pair of opposed projections extending from the outer surface of said main housing and that may be manually engaged and axially moved by a user.

11. The multiple use needle-less injection device of claim 7 wherein said nozzle includes means for locking within said main housing in response to axially applied forward urging thereof, and said nozzle retainer when securing said nozzle to said main housing applies constant forwardly directed axial force against said nozzle maintaining said nozzle locked inside said main housing.

12. The multiple use needle-less injection device of claim 11 further including a coil compression spring pushing forwardly said nozzle retainer.

13. The multiple use needle-less injection device of claim 7 further including means to removably attach said nozzle to a medicament vial, said means for removably attaching to said vial including:

said nozzle having plural protruding tabs at a forward end thereof; and a vial head including plural tabs protruding toward said nozzle, and plural side openings on the circumference of the vial head, said side openings including two or more flexible arms circumscribing and locking on said protruding tabs of said nozzle as said medicament vial head is engaged and twisted over the said nozzle.

14. A multiple use needle-less hypodermic injection device for injecting liquid medicament subcutaneously of human skin in a high velocity unconstrained liquid jet; said injection device comprising:

a housing containing a movable ram reciprocable axially along its longitudinal axis, an energy accumulator in said housing and when released driving said ram forcefully forward, said housing having a discharge mechanism both for storing energy in said energy accumulator in response to manual manipulation of said housing when cocked, and for releasing said accumulator mechanism to effect a medicament injection when triggered; said discharge mechanism including an axially movable discharge shaft forward axial movement of which effects release of said accumulator mechanism, said discharge shaft having a crowned end surface, a trigger mechanism in juxtaposition with said end surface of said discharge shaft and including a first ball member axially spaced from and aligned with said crowned surface, a second ball member carried in a laterally movable member having a portion extending outwardly of said housing to define a trigger push button, said second ball member having a diameter larger than a certain axial spacing between said crowned surface and said first ball member when said discharge mechanism is cocked, and lateral manual movement of said push button to trigger said discharge mechanism forcing said second ball member in rolling contact between said crowned surface and said first ball member to move said discharge shaft axially and trigger said discharge mechanism.

15. A disposable medicament vial especially configured for tamper resistance and for sealing interface with a needle-less injection device, said vial comprising:

an ampule having a body defining a chamber therein and an opening from said chamber with an outwardly extending rim circumscribing said opening;

a polymer stopper received into said opening and closing said chamber, said stopper having an outwardly extending flange portion overlying said rim of said ampule and a penetrable septum portion centrally located thereof;

a molded polymer head received on said stopper, said head including a base portion with an outwardly extending rim seated upon said flange portion of said stopper and in axial congruent juxtaposition to said rim of said ampule, said base portion carrying a medicament inlet needle penetrating said penetrable septum of said stopper and opening at a beveled end thereof into said chamber; said base portion outwardly carrying an elastomeric disc having a center hole with which an opposite end of said inlet needle communicates; said base portion outwardly including means for securing to a nozzle of a needle-less injection device so as to communicate an injection orifice of the device with the center hole of the elastomeric disc to aspirate medicament from said ampule into the injection device via said inlet needle;

said head further including a tamper resistant frangible plastic cap received over said means for securing said base portion to an injection device and obstructing access to said elastomeric disc, said cap also having a respective outwardly extending rim circumscribing said base portion and in axial congruent juxtaposition to both said rim of said base portion and said rim of said ampule, said cap having frangible means for separating a distal portion of said cap from said rim thereof, and a malleable metal band circumscribing both said ampule, said stopper, said base portion, and said cap at each said rim, said band being crimped into permanent engagement with each rim of said ampule and of said cap, capturing said rim of said base portion and said flange of said stopper therebetween.

* * * * *